(12) United States Patent
Somberg

(10) Patent No.: US 12,343,320 B2
(45) Date of Patent: Jul. 1, 2025

(54) INTRAVENEOUS DOFETILIDE TO REDUCE THE RISK OF DEVELOPING AF/AFL POST CORONARY BYPASS SURGERY

(71) Applicant: Hyloris Developments SA, Liège (BE)

(72) Inventor: John Somberg, Lake Forest, IL (US)

(73) Assignee: Hyloris Developments SA, Liege (BE)

( * ) Notice: Subject to any disclaimer, the term of this patent is extended or adjusted under 35 U.S.C. 154(b) by 0 days.

(21) Appl. No.: 18/162,092

(22) Filed: Jan. 31, 2023

(65) Prior Publication Data

US 2024/0252455 A1   Aug. 1, 2024

(51) Int. Cl.
*A61K 31/18* (2006.01)
*A61K 9/00* (2006.01)
*A61P 9/06* (2006.01)

(52) U.S. Cl.
CPC ............ *A61K 31/18* (2013.01); *A61K 9/0019* (2013.01); *A61K 9/0053* (2013.01); *A61P 9/06* (2018.01)

(58) Field of Classification Search
CPC .... A61K 31/18; A61K 9/0019; A61K 9/0053; A61P 9/06
See application file for complete search history.

(56) References Cited

U.S. PATENT DOCUMENTS

| 11,364,213 | B2 | 6/2022 | Somberg | |
|---|---|---|---|---|
| 2021/0346325 | A1* | 11/2021 | Somberg | A61K 9/08 |
| 2023/0172883 | A1* | 6/2023 | Kashfian | A61K 31/18 |
| | | | | 514/603 |

OTHER PUBLICATIONS

Frost et al. Efficacy and safety of dofetilide, a new class III antiarrhythmic agent, in acute termination of atrial fibrillation or flutter after coronary artery bypass surgery, International Journal of Cardiology, 58:135-140 (Year: 1997).*
Walpole et al. The weight of nations: an estimation of adult human biomass, BMC Public Health, 12: 439 (Year: 2012).*
U.S. Appl. No. 18/176,017 Office Action mailed Sep. 13, 2023.
U.S. Appl. No. 18/175,971 Office Action mailed Sep. 11, 2023.
Singh, S. et al., Efficacy and Safety of Oral Dofetilide in Converting to and Maintaining Sinus Rhythm in Patents With Chronic Atrial Fibrillation or Atrial Flutter, Circulation 2000, 7, 2385-2390.
Zou, H. et al., Application of Pharmacokinetic-Pharmacodynamic Modeling in Drug Delivery: Development and Challenges, Fontiers in Pharmacology 2020, 11, 997.
January, C.T. et al., 2014 AHA/ACC/HRS Guideline for the Management of Patients with Atrial Fibrillation, Circulation 2014, 130(23), e199-267.

* cited by examiner

*Primary Examiner* — Joseph K McKane
*Assistant Examiner* — Meghan C Heasley
(74) *Attorney, Agent, or Firm* — Vance Intellectual Property, PC

(57) ABSTRACT

The present invention involves a novel method of reducing the risk of developing atrial fibrillation (AF) and/or atrial flutter (AFL) post coronary bypass surgery (CABS) by administering, to patients who have undergone CABS, loading and maintenance doses of dofetilide intravenously followed by oral doses.

23 Claims, 1 Drawing Sheet

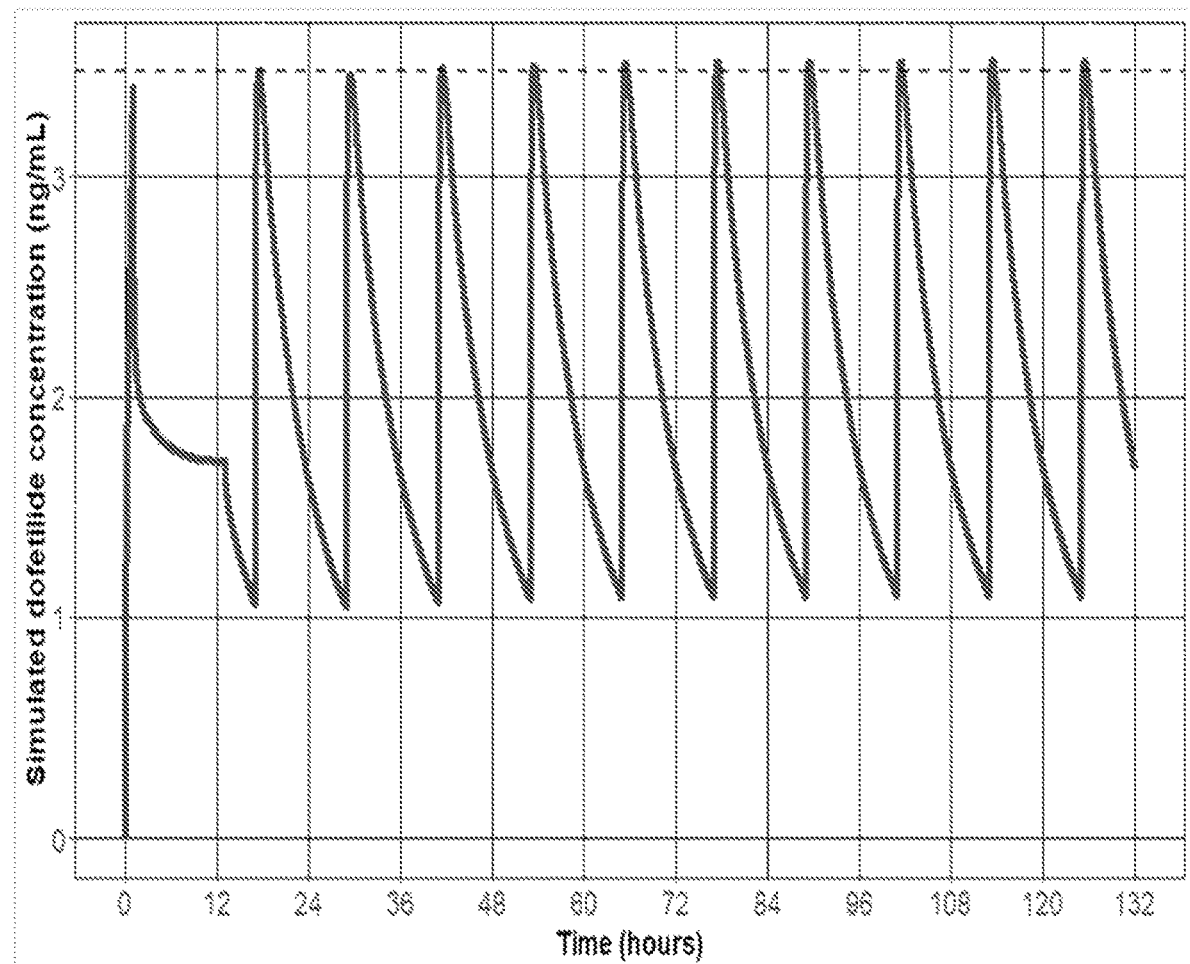

INTRAVENEOUS DOFETILIDE TO REDUCE THE RISK OF DEVELOPING AF/AFL POST CORONARY BYPASS SURGERY

FIELD OF THE INVENTION

The present invention involves a novel method of reducing the risk of developing atrial fibrillation (AF) and/or atrial flutter (AFL) post coronary bypass surgery (CABS) by administering dofetilide intravenously to patients who have undergone CABS.

BACKGROUND OF THE INVENTION

Dofetilide is an anti-arrhythmic of the Vaughn Williams Class III. Its action is to prolong the action potential duration, specifically by prolonging repolarization time. Dofetilide does this by blocking the outward potassium channel IKr (rapid potassium rectifier current). This action is both anti-arrhythmic and pro-arrhythmic. Excessive prolongation of the repolarization time may give rise to life threatening arrhythmias, especially those called Torsade de Pointe ventricular tachycardia (Tpd). The repolarization time of cardiac cells may be manifest on the body surface ECG (electrocardiogram) by an increase in the QT interval. Since the QT interval varies with heart rate, often the QT interval is measured as the heart rate corrected QT, called the $QT_c$. Prolongation of the $QT_c$ interval by pharmaceutical agents may give rise to arrhythmias. Thus, in the initial loading phase, or in a dose escalation procedure, it is critical to monitor the $QT_c$ interval to avoid excessive $QT_c$ prolongation and thus the possible development of life threatening ventricular tachycardia's, especially those of the Tdp variety. For these reasons the FDA has mandated in-hospital $QT_c$ monitoring in initial dofetilide loading or for dose escalation. But, for a patient in need of chronic dofetilide therapy (e.g., a patient who presents with intermittent AF but who is in current sinus rhythm), it takes at least 3 days for oral dofetilide to reach a steady state concentration and thus for the concentration to be reflected in full expression in $QT_c$ prolongation. Patients, therefore, typically require a 3 day hospital stay to prevent endangering themselves to possible arrhythmias occurring outside the hospital where help is often not available.

The relationship between blood concentration of dofetilide and $QT_c$ can be expressed as: $QT_c$=baseline $QT_c$+ (slope relationship×blood dofetilide concentration). The relationship between dofetilide plasma concentration and $QT_c$ has been previously established. The $QT_c$ changes between 15-25 msec/ng/mL (average=20 msec) as reported by Sedgwick et al, Br J. Clin Pharmacol 1991:31:515-519. Thus, for a patient with an initial $QT_c$ of 405 msec QT who received an IV dose of 2.4 µg/kg, which would be analogous to a chronic dose of 500 µg bid, it would be expected to show a $QT_c$ of 459 msec on average, a 13% increase over baseline, within acceptable limits.

$$QT_c = 405 \ msec + (20 \ msec/ng/mL \times 2.7 \ ng/mL) = 459 \ msec$$

When administering dofetilide, a physician first assesses the $QT_c$ interval. If the $QT_c$ is greater than 440 msec (500 msec in patients with ventricular conduction abnormalities), dofetilide is not indicated. The physician then calculates the patient's creatinine clearance (CrCl, which is a useful approximation of the glomerular filtration rate (GFR)) employing the following formulas:

Creatinine clearance (male) =

$$((140 - Age) \times Body \ Wt(kg))/(72 \times serum \ creatinine \ (mg/dL))$$

Creatinine clearance (female) = Creatine clearance (male) × 0.85

Following calculation of CiCl, the starting dose of dofetilide is determined as shown below.

| Creatinine Clearance (CrCl) | Starting Dose of Dofetilide |
| --- | --- |
| 60 mL/min or more | 500 µg bid |
| 40-<60 mL/min | 250 µg bid |
| 20-<40 mL/min | 125 µg bid |
| <20 mL/min | Dofetilide not indicated |

The physician then must monitor the $QT_c$ till steady state is achieved, in this case 5-6 doses, or 3 days in hospital with ECG monitoring. This is a costly, time intensive procedure and impractical when the goal is to rapidly load dofetilide to prevent AF/AFL in the immediate post-operative period.

U.S. Pat. No. 11,364,213 (US '213) involves a method of reducing the 3-day loading period for patients in need of chronic, oral dofetilide. Generally, these patients, who typically present with intermittent AF but are in current sinus rhythm, are given a first intravenous dofetilide dose followed by twice daily (BID) oral dofetilide. US '213 describes how the claimed method can assess the risk of dofetilide in the patient in one day or less, thereby reducing costs. e.g., hospital costs, for initiating chronic oral dofetilide therapy.

In the United States there are approximately four hundred thousand open heart coronary bypass operations a year and an additional 100,000 cardiac valve surgeries. Due to opening the pericardial cavity, the manipulation of the heart and the placing of temporary atrial pacing leads there is between a 30-50% incidence of post-operative AF/AFL 3 to 5 days post-operative. AF/AFL can be very rapid causing symptoms and hemodynamic patient compromise. AF/AFL post-operatively can cause serious complications and significantly prolong the patient's hospitalization.

Dofetilide is an effective agent that can prevent AF/AFL. However, the time necessary to load dofetilide orally, the only currently approved method of administration, makes its use less effective in preventing early onset AF/AFL. An IV loading dose could quickly obtain an effective concentration. However, dofetilide can cause QT prolongation that can, when excessive, lead to the development of life threatening ventricular arrhythmias.

Therefore, it would be beneficial to develop a method of using dofetilide to prevent AF and/or AFL in patients undergoing open heart coronary bypass.

SUMMARY OF THE INVENTION

Accordingly, in an aspect, the present invention involves a novel method of intravenously loading and maintaining dofetilide in a patient following coronary artery bypass surgery with the goal to reduce the risk of AF/AFL from developing post-surgery.

In another aspect, the method involves intravenously administering a loading dose and maintenance dose of dofetilide with a switch-over to oral dose maintenance.

These and other objects, which will become apparent during the following detailed description, have been achieved by the inventors' discovery that intravenous dofetilide can be used to inhibit/prevent AF/AFL in a patient following coronary artery bypass surgery.

BRIEF DESCRIPTION OF THE DRAWINGS

FIG. 1 shows a graph of the estimated blood dofetilide concentration obtained with the dosage regimen of Example 1.

DETAILED DESCRIPTION OF THE INVENTION

All references cited herein are hereby incorporated in their entirety herein by reference.
Definitions
About is defined as +/−10% of the numerical value.
BID or bid or b.i.d. refers to twice-daily or once every 12 hours.
BP is blood pressure.
HR is heart rate.
IV means intravenous or intravenously.
Dofetilide
Prior studies have reported that a single dose of dofetilide, following a 10 min. infusion of 1.5 μg/kg yielded a peak plasma concentration of 1.74 ng/mL. (Sedgwick et al, Br. J. Clin Pharmacol 1991:31:515-519 and Rasmussen et al J. Cardiovascular Pharmacology 20:1992, S96-101.) An infusion of 3.0 μg/mL resulted in a plasma concentration of 5.35 ng/mL. (Sedgwick et al. and Rasmussen et al.) Coz and associates (Clin. Pharmacology & Therapeutics, 1995; 57(5) 533-54) reported that a 500 μg oral dose of dofetilide yielded a plasma concentration Cmax of 1.9 ng/mL. Thus, if a single dose reaches 70% of predicted steady state, at steady state, one can estimate Cmax ss to be 2.7 ng/mL, if 500 μg/mL was administered twice daily for at least 5 doses. If an IV dose of 1.5 μg/kg is known to result in a peak level of 1.7 ng/mL, a dose of 2.4 μg/kg, assuming linear kinetics, would reach a peak concentration of 2.7 ng/mL, exposing the patient to the peak serum concentration predicted for steady state and thus the maximum $QT_c$ prolongation. This would fully expose the patient to the potentially greatest arrhythmic risk in a short period of time, while monitored in hospital.

IV dofetilide kinetics are linear permitting a direct relationship between IV dose of dofetilide administered and serum concentration obtained. With IV administration one can avoid "overshoot" in serum concentration, avoiding excessive dofetilide blood levels and thus possible arrhythmias. The relationship between serum concentration and $QT_c$ interval is well known, with a high degree of correlation.
CABS: Coronary Bypass Surgery
It is generally preferred that the heart undergoing surgery is not exposed to unnecessary anti-arrhythmic drugs that could lead to adverse outcomes. It is also known that there is a 30-50% incidence of a CABS patient developing atrial fibrillation (AF) and/or atrial flutter (AFL) 3 to 5 days post-operative.

In view of the above, the present invention involves a novel method of loading dofetilide to maximize patient safety by carefully obtaining a minimally requisite effective drug blood concentration ensuring that there is no excessive QT prolongation that can result in cardiac repolarization abnormalities resulting in life threatening ventricular arrhythmias.

Thus, in an aspect, the present invention involves a novel method of reducing the risk of developing AF and/or AFL post CABS by administering dofetilide intravenously to patients who have undergone CABS. In another aspect, the method involves intravenously administering a loading dose of dofetilide and intravenously administering a maintenance dose of dofetilide. In another aspect, the method involves orally administering dofetilide BID. In another aspect, the method involves intravenously administering a loading dose and at least one maintenance dose of dofetilide with switchover to oral dose maintenance.

Reducing the risk refers to reducing 30-50% risk of developing AF/AFL 3-5 post CABS surgery. Examples include reducing the risk to about 25, 20, 15, 10, 5, 4, 3, 2, 1, to 0% of developing AF and/or AFL.

In another aspect, the present invention involves a novel method of reducing the risk of developing atrial fibrillation (AF) and/or atrial flutter (AFL) in a patient who has undergone coronary bypass surgery (CABS), comprising:

a measuring the $QT_c$ of the patient to establish a baseline $QT_c$ and then measuring the $QT_c$ about every 15-30 minutes thereafter;

b intravenously administering a loading dose of dofetilide to the patient who has undergone CABS, wherein:
(A) the loading dose is about 450-500 μg of dofetilide; and,
(B) the loading dose is administered over about 30-60 minutes;

c about 0-4 h after completion of the IV loading dose, intravenously administering a maintenance dose of dofetilide over about 12 h, the maintenance dose given being based on the creatinine clearance of the CABS patients as given in the following table;

| Creatinine Clearance (CrCl) | IV Maintenance Dofetilide Dose (12 h) |
|---|---|
| 60 mL/min or more | 450-500 μg |
| 40-<60 mL/min | 225-250 μg |
| 20-<40 mL/min | 100-125 μg |
| <20 mL/min | Dofetilide not indicated | d once the patient has recovered enough from CABS to take dofetilide orally, stopping the IV maintenance dose.

In another aspect, the method, further comprises:
e about 2-6 h after stopping the maintenance dose, orally administering dofetilide every 12 h, the oral dose given being based on the creatinine clearance of the CABS patients as given in the following table;

| Creatinine Clearance (CrCl) | Oral Dose of Dofetilide |
|---|---|
| 60 mL/min or more | 500 μg bid |
| 40-<60 mL/min | 250 μg bid |
| 20-<40 mL/min | 125 μg bid |
| <20 mL/min | Dofetilide not indicated | provided that if the patient's QTc increases by 15% over the baseline QTc or if the QTc is measured at >500 msec or >550 msec in patients with ventricular conduction abnormalities, the oral doses of dofetilide are reduced to 250 μg from 500 μg, 125 μg from 250 μg, or discontinued if originally 125 μg.

Typically, the $QT_c$ is measured prior to administration of dofetilide to establish a baseline $QT_c$ against which further $QT_c$ measurements can be compared. The $QT_c$ is typically measured about every 15, 20, 25, to 30 minutes. These measurements can be discontinued once the patient's medical staff is confident that the patient is stabilized on dofetilide. For example, the $QT_c$ measurements can be discontinued after the maintenance dose of dofetilide is discontinued. Alternatively, the $QT_c$ measurements can be discontinued after enough oral doses have been administered. The healthcare provided can determine when to discontinue the $QT_c$ measurements. Examples of a sufficient number of oral doses include 1, 2, 3, 4, 5, 6, 7, 8, 9, 10, 11, 12, 13, 14, 15, 16, 17, 18, 19, to 20 oral doses.

In another aspect, the patient is monitored via electrocardiography to determine the patient's $QT_c$.

The IV loading dose is typically about 450-500 µg of dofetilide. Examples include about 450, 455, 460, 465, 470, 475, 480, 485, 490, 495, to 500 µg of dofetilide. Typically, the loading dose chosen is an amount that achieves the predicted maximal serum concentration from orally administering 500 µg dofetilide.

The IV loading dose is typically given over about 30-60 minutes. Examples include about 30, 31, 32, 33, 34, 35, 36, 37, 38, 39, 40, 30, 41, 42, 43, 44, 45, 46, 47, 48, 49, 50, 30, 51, 52, 53, 54, 55, 56, 57, 58, 59, to 60 minutes.

In another aspect, the IV maintenance dose is started upon completion of the loading dose. In another aspect, the IV maintenance dose is started about 0, 0.5, 1, 1.5, 2, 2.5, 3, 3.5, 4, 4.5, 5, 5.5, to 6 h after completion of the loading dose.

The IV maintenance dose, which typically is given for about 12 h, can be discontinued at any time. In another aspect, the maintenance dose is administered for about 1, 2, 3, 4, 5, 6, 7, 8, 9, 10, 11, 12, 13, 14, 15, 16, 17, 18, 19, 20, 21, 22, 23, to 24 h. Additional examples include about 1.5, 2, 2.5, 3, 3.5, to 4 days (or sometimes longer).

The IV maintenance dose can be discontinued if needed (e.g., an elevated $QT_c$ is measured). This is an advantage of an IV versus an oral dose. The IV dose can be quickly stopped if the patient is having an adverse effect to the dofetilide.

The IV maintenance dose given is dependent upon the CrCl of the patient, as shown in the table below.

| Creatinine Clearance (CrCl) | IV Maintenance Dofetilide Dose (12 h) |
|---|---|
| 60 mL/min or more | 450-500 µg |
| 40-<60 mL/min | 225-250 µg |
| 20-<40 mL/min | 100-125 µg |
| <20 mL/min | Dofetilide not indicated |

For a patient with a CrCl of ≥60 mL/min, the IV maintenance dose is typically about 450-500 µg of dofetilide and is typically given over about 12 h (but can vary as noted above). Examples include about 450, 455, 460, 465, 470, 475, 480, 485, 490, 495, to 500 µg of dofetilide. This equates to about 0.625-0.694 µg/min of dofetilide (450/720 to 500/720). In another aspect, the IV maintenance dose is about 0.6, 0.61, 0.62, 0.63, 0.64, 0.65, 0.66, 0.67, 0.68, 069, to 0.7 µg/min.

For a patient with a CrCl of 40-<60 mL/min, the IV maintenance dose is typically about 225-250 µg of dofetilide and is typically given over about 12 h (but can vary as noted above). Examples include about 225, 230, 235, 240, 245, to 250 µg of dofetilide. This equates to about 0.313-0.347 µg/min of dofetilide (225/720 to 250/720). In another aspect, the IV maintenance dose is about 0.3, 0.31, 0.32, 0.33, 0.34, to 0.35 µg/min.

For a patient with a CrCl of 20-<40 mL/min, the IV maintenance dose is typically about 100-125 µg of dofetilide and is typically given over about 12 h (but can vary as noted above). Examples include about 100, 105, 110, 115, 120, to 125 µg of dofetilide. This equates to about 0.139-0.174 µg/min of dofetilide (100/720 to 125/720). In another aspect, the IV maintenance dose is about 0.13, 0.14, 0.15, 0.16, 0.17, to 0.18 µg/min.

Since a patient is not awake during CABS and shortly after CABS, oral dofetilide cannot be administered. So, one advantage of the present invention is that a patient having undergone CABS can be loaded with dofetilide before the patient would normally be capable of taking oral dofetilide. Once a patient is determined to have recovered enough from CABS to take dofetilide orally, the dofetilide IV maintenance dose can be discontinued and a switch-over to oral dofetilide realized. It is the patient's medical staff (e.g., surgeon, doctor, nurse, etc.) that determines when a patient can take dofetilide orally. Typically, a patient can take oral medication when they are coherent. In some aspects, this will be when the patient awakens after surgery. In other aspects, the patient may require more time after waking up to be sufficiently coherent and able to swallow a pill.

In another aspect, the oral dose is started about 1, 2, 3, 4, 5, 6, 7, 8, 9, to 10 hours after the maintenance dose has been stopped. In another aspect, the oral dose is started about 3-6 hours after the maintenance dose has been stopped.

Oral dofetilide is available in capsule form in three sizes, 125, 250, and 500 µg. In another aspect, the patient is given dofetilide orally BID (once every 12 hours). Examples of these doses include 125, 250, 375 (e.g., 3×125 capsules or 125+250 capsules), and 500 µg.

The standard dose for patients having a creatinine clearance (CrCl)(or calculated GFR (glomerular filtration rate)) of ≥60 mL/min is 500 µg. However, per the table below, this dose is lowered if the patient's CRCL is <60 mL/min.

| Creatinine Clearance (CrCl) | Starting Oral Dose of Dofetilide |
|---|---|
| 60 mL/min or more | 500 µg bid |
| 40-<60 mL/min | 250 µg bid |
| 20-<40 mL/min | 125 µg bid |
| <20 mL/min | Dofetilide not indicated |

The oral dose of dofetilide is also reduced if warranted by the patient's $QT_c$. For example, if the patient's $QT_c$ increases by 15% over the baseline $QT_c$ or if the $QT_c$ is measured at >500 msec or >550 msec in patients with ventricular conduction abnormalities, the oral dose of dofetilide is reduced to 250 µg from 500 µg, or 125 µg from 250 µg, or discontinued if the original dose was 125 µg.

For a patient with a CrCl of ≥60 mL/min, the twice-daily oral doses of dofetilide are 500 µg. In this aspect, the oral doses are reduced to 250 µg if the patient's $QT_c$ increased by 15% over baseline $QT_c$ or if the QTc is measured at >500 msec or >550 msec if the patient has a ventricular conduction abnormality.

For a patient with a CrCl of 40-<60 mL/min, the twice-daily oral doses of dofetilide are 250 µg. In this aspect, the oral doses are reduced to 125 µg if the patient's $QT_c$ increased by 15% over baseline $QT_c$ or if the QTc is measured at >500 msec or >550 msec if the patient has a ventricular conduction abnormality.

For a patient with a CrCl of 20-<40 mL/min, the twice-daily oral doses of dofetilide are 125 µg. In this aspect, the treatment is discontinued if the patient's $QT_c$ is increased by 15% over baseline $QT_c$ or if the QTc is measured at >500 msec or >550 msec if the patient has a ventricular conduction abnormality.

In an alternative aspect, a patient with a CrCl of 20-<40 mL/min is given 125 µg of dofetilide orally once daily. This once-daily regimen is selected based on the judgment of the patient's health care provider (e.g., physician, surgeon, doctor, etc.). In this aspect, the treatment is discontinued if the patient's $QT_c$ is increased by 15% over baseline $QT_c$ or if the QTc is measured at >500 msec or >550 msec if the patient has a ventricular conduction abnormality.

In another aspect, the patient has a CrCl of ≥60 mL/min, the IV maintenance dose is about 450-500 µg of dofetilide and is given over about 12 h and the twice-daily oral doses of dofetilide are 500 µg. In this aspect, the oral doses are reduced to 250 µg if the patient's $QT_c$ increased by 15% over baseline $QT_c$ or if the QTc is measured at >500 msec or >550 msec if the patient has a ventricular conduction abnormality.

In another aspect, the patient has a CrCl of 40-<60 mL/min, the IV maintenance dose is about 225-250 µg of dofetilide and is given over about 12 h and the twice-daily oral doses of dofetilide are 250 µg. In this aspect, the oral doses are reduced to 125 µg if the patient's $QT_c$ increased by 15% over baseline $QT_c$ or if the QTc is measured at >500 msec or >550 msec if the patient has a ventricular conduction abnormality.

In another aspect, the patient has a CrCl of 20-<40 mL/min, the IV maintenance dose is about 100-125 µg of dofetilide and is given over about 12 h and the twice-daily oral doses of dofetilide are 125 µg. In this aspect, the treatment is discontinued if the patient's $QT_c$ is increased by 15% over baseline $QT_c$ or if the QTc is measured at >500 msec or >550 msec if the patient has a ventricular conduction abnormality.

In an alternative aspect, the patient has a CrCl of 20-<40 mL/min, the IV maintenance dose is about 100-125 µg of dofetilide and is given over about 12 h, and the once-daily oral dose of dofetilide is 125 µg. In this aspect, the treatment is discontinued if the patient's $QT_c$ is increased by 15% over baseline $QT_c$ or if the QTc is measured at >500 msec or >550 msec if the patient has a ventricular conduction abnormality.

Suitable intravenous formulations are described in U.S. Pat. No. 11,364,213.

Examples of the concentration of a useful dofetilide intravenous solution includes about 1, 2, 3, 4, 5, 10, 15, 20, 25, 30, 35, 40, 45, 50, 55, 60, 65, 70, 75, 80, 85, 90, 95 to 100 µg/mL.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Other features of the invention will become apparent in the course of the following descriptions of exemplary embodiments that are given for illustration of the invention and are not intended to be limiting thereof.

EXAMPLES

Example 1

A 70 kg patient with a CrCl>90 mL/min presents after coronary bypass surgery. To decrease the possibility of AF post-op the patient is to receive a loading dose of dofetilide after the surgery is completed. The patient has an ECG continuously monitored. The patient is then subjected to the following treatment with dofetilide.

(A) Hour 0: Intravenous (IV) Loading Dose: 450 µg, infusion over 1 h measuring $QT_c$, HR, and BP every 15 minutes;

(B) Hour 1: IV Maintenance Dose: 450 µg, 12 h infusion, started at the end of the loading dose infusion; and, (C) Hour 16: Oral Dose: 500 µg given orally every 12 hours (BID), started 3 h after termination of IV maintenance infusion.

The FIG. 1 shows the estimated blood dofetilide concentration obtained with the above described dosage regimen. The graph in FIG. 1 was obtained by modeling the above dosage regimen. The software packages NONMEM™ version 7.4 (ICON, Hanover, MD, USA) and MWpharm (Mediware, Prague, CZ)6 were used for the Bayesian PK modeling. PsN7 (Dept. of Pharmacy, Uppsala University, Uppsala, Sweden) was used for automation procedures. R (version 3.5.1, The R Foundation for Statistical Computing) was used for data preparation, graphical analysis, linear regression analysis, and statistical summaries. R package 'mrgsolve' was used for simulations.

Step (A): the loading dose, which in this example is a 450 µg IV infusion of dofetilide over 1 h, is expected to achieve the predicted maximal serum concentration that one would expect from 500 µg-dofetilide orally. This would reach peak, if administered orally, after 6 doses twice daily of dofetilide. The peak concentration will typically be reached at termination of infusion.

$QT_c$ would be measured every 15 mins.

Step (B): the IV maintenance dose of a 450 µg IV infusion of dofetilide over 12 h (0.625 µg/min) is initiated at the end of the 1 h loading IV. This dose can be maintained until the patient is awake and able to take dofetilide orally.

Once the patient can take dofetilide orally, the dofetilide maintenance IV is stopped. Starting about 3 h after stopping the maintenance IV, an oral dose of 500 µg of dofetilide is administered every 12 h (BID).

If the $QT_c$ has increased by 15% over baseline $QT_c$ or if a $QT_c$>500 msec is observed (550 msec in patients with ventricular conduction abnormalities), subsequent oral doses would be reduced to 250 µg BID (or lower if the original oral dose called for is lower, see below).

It is noted that if patients present with a lower than normal CrCl, the initial target concentration would be the same, but the oral (maintenance) dose administered would be lower; 250 µg or 125 µg BID (based on the chart below).

| Creatinine Clearance (CrCl) | Oral Dose of Dofetilide |
| --- | --- |
| 60 mL/min or more | 500 µg bid |
| 40-<60 mL/min | 250 µg bid |
| 20-<40 mL/min | 125 µg bid |
| <20 mL/min | Dofetilide not indicated |

Further, in patients that show excessive $QT_c$ prolongation at initial loading (>500 msec or >550 msec in patients with ventricular conduction abnormalities), the first oral dose would be reduced to 250 µg (or 125 µg if starting oral dose was 250 µg based on the above chart) and the peak concentration expected in 4 h with $QT_c$ re-evaluated. In this way, a concentration projection from a dofetilide chronic oral dosing of 250 µg could be readily evaluated, with $QT_c$ observation.

Example 2

A 75 kg patient with a CrCl of 45 mL/min is undergoing CABGS presents after coronary bypass surgery. To decrease the possibility of AF post-op the patient is to receive a loading dose of dofetilide after the surgery is completed. The patient has an ECG continuously monitored. The patient is then subjected to the following treatment with dofetilide.
- (A) Hour 0: IV Loading Dose: 450 μg, infusion over 1 h measuring $QT_c$, HR, and BP every 15 minutes.
- (B) Hour 4: Maintenance Infusion: 225 μg infused over 12 hours started 3 hours after the end of the IV Loading Dose.
- (C) Hour 21: Oral Dose initiated 250 μg given orally every 12 hours, started 5 hours after termination of IV maintenance infusion.

Numerous modifications and variations of the present invention are possible in light of the above teachings. It is therefore to be understood that within the scope of the appended claims, the invention may be practiced otherwise than as specifically described herein.

What is claimed is:

1. A method of reducing the risk of developing atrial fibrillation (AF) and/or atrial flutter (AFL) in a patient who has undergone coronary bypass surgery (CABS), and who has a creatinine clearance (CrCl) of 60 mL/min or higher, 40-<60 mL/min or 20-<40 mL/min, comprising:
   a measuring the $QT_c$ of the patient who has undergone CABS to establish a baseline $QT_c$ and then measuring the $QT_c$ about every 15-30 minutes thereafter;
   b intravenously administering a loading dose of dofetilide to the patient who has undergone CABS, wherein:
   (A) the loading dose is about 450-500 μg of dofetilide; and,
   (B) the loading dose is administered over about 30-60 minutes;
   c about 0-4 h after completion of the IV loading dose, intravenously administering a maintenance dose of dofetilide over about 12 h, the maintenance dose given being based on the creatinine clearance (CrCl) of the CABS patient as given in the following table;

| CrCl | IV Maintenance Dose | Oral Dose |
|---|---|---|
| 60 mL/min or higher | 450-500 μg | 500 μg |
| 40-<60 mL/min | 225-250 μg | 250 μg |
| 20-<40 mL/min | 100-125 μg | 125 μg | d when the patient's medical staff determines the patient can take dofetilide orally, stopping the IV maintenance dose and QTc measuring; and,
   e about 2-6 h after stopping the IV maintenance dose, orally administering dofetilide every 12 h, the oral dose given being based on the CrCl of the patient who has undergone CABS as given in the above table;
   provided that if the patient's QTc increases by 15% over the baseline QTc or if the QTc is measured at >500 msec or >550 msec if the patient has a ventricular conduction abnormality, the oral dose is reduced to 250 μg from 500 μg, 125 μg from 250 μg, or discontinued if originally 125 μg;
   thereby reducing the risk of developing AF and/or AFL in the CABS patient 3-5 days post-operative.

2. The method of claim 1, wherein the loading dose is about 450 μg.

3. The method of claim 1, wherein the loading dose is about 460 μg.

4. The method of claim 1, wherein the loading dose is about 470 μg.

5. The method of claim 1, wherein the loading dose is about 480 μg.

6. The method of claim 1, wherein the loading dose is about 490 μg.

7. The method of claim 1, wherein the loading dose is about 500 μg.

8. The method of claim 1, wherein the loading dose is administered over about 30 minutes.

9. The method of claim 1, wherein the loading dose is administered over about 40 minutes.

10. The method of claim 1, wherein the loading dose is administered over about 50 minutes.

11. The method of claim 1, wherein the loading dose is administered over about 60 minutes.

12. The method of claim 1, wherein the maintenance dose is started about 0 h after completion of the loading dose.

13. The method of claim 1, wherein the maintenance dose is started about 1 h after completion of the loading dose.

14. The method of claim 1, wherein the maintenance dose is started about 2 h after completion of the loading dose.

15. The method of claim 1, wherein the maintenance dose is started about 3 h after completion of the loading dose.

16. The method of claim 1, wherein the maintenance dose is started about 4 h after completion of the loading dose.

17. The method of claim 1, wherein the patient has a CrCl of ≥60 mL/min, the IV maintenance dose is about 450-500 μg given over about 12 h and the oral doses are 500 μg.

18. The method of claim 17, wherein the oral doses are reduced to 250 μg due to a $QT_c$ that increased by 15% over baseline $QT_c$ or if the QTc is measured at >500 msec or >550 msec if the patient has a ventricular conduction abnormality.

19. The method of claim 1, wherein the patient has a CrCl of 40-<60 mL/min, the IV maintenance dose is about 225-250 μg given over about 12 h and the oral doses are 250 μg.

20. The method of claim 19, wherein the oral doses are reduced to 125 μg due to a $QT_c$ that increased by 15% over baseline $QT_c$ or if the QTc is measured at >500 msec or >550 msec if the patient has a ventricular conduction abnormality.

21. The method of claim 1, wherein the patient has a CrCl of 20-<40 mL/min, the IV maintenance dose is about 100-125 μg given over about 12 h and the oral doses are 125 μg.

22. The method of claim 21, wherein the oral doses are discontinued due to a $QT_c$ that increased by 15% over baseline $QT_c$ or if the QTc is measured at >500 msec is observed or >550 msec if the patient has a ventricular conduction abnormality.

23. A method of reducing the risk of developing atrial fibrillation (AF) and/or atrial flutter (AFL) in a patient who has undergone coronary bypass surgery (CABS) and who has a creatinine clearance (CrCl) of 20-<40 mL/min, comprising:
   a measuring the $QT_c$ of the patient who has undergone CABS to establish a baseline $QT_c$ and then measuring the $QT_c$ about every 15-30 minutes thereafter;
   b intravenously administering a loading dose of dofetilide to the patient who has undergone CABS, wherein:
   (A) the loading dose is about 450-500 μg of dofetilide; and,
   (B) the loading dose is administered over about 30-60 minutes;

c about 0-4 h after completion of the IV loading dose, intravenously administering a 100-125 μg maintenance dose of dofetilide over about 12 h, this maintenance dose being based on the CrCl of the CABS patient;

f stopping the IV maintenance dose and QTc measuring when the patient's medical staff determines the patient can take dofetilide orally; and, d about 2-6 h after stopping the IV maintenance dose, orally administering 125 μg of dofetilide every 24 h;

provided that if the patient's QTc increases by 15% over the baseline QTc or if the QTc is measured at >500 msec or >550 msec if the patient has a ventricular conduction abnormality, the oral dose is discontinued;

thereby reducing the risk of developing AF and/or AFL in the CABS patient 3-5 days post-operative.

* * * * *